US008984282B1

(12) United States Patent
Kragh

(10) Patent No.: US 8,984,282 B1
(45) **Date of Patent: *Mar. 17, 2015**

(54) IDENTITY VALIDATION AND VERIFICATION SYSTEM AND ASSOCIATED METHODS

(71) Applicant: James F. Kragh, Winter Park, FL (US)

(72) Inventor: James F. Kragh, Winter Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/898,669

(22) Filed: May 21, 2013

Related U.S. Application Data

(63) Continuation-in-part of application No. 12/792,980, filed on Jun. 3, 2010, now Pat. No. 8,464,046.

(60) Provisional application No. 61/183,600, filed on Jun. 3, 2009.

(51) Int. Cl.
*H04L 29/06* (2006.01)
*H04L 9/32* (2006.01)

(52) U.S. Cl.
CPC .................................... *H04L 9/321* (2013.01)
USPC .................. 713/156; 713/186; 705/3; 705/38

(58) Field of Classification Search
USPC ......................................... 713/156; 705/2, 3
See application file for complete search history.

(56) References Cited

U.S. PATENT DOCUMENTS

| | | | |
|---|---|---|---|
| 6,892,679 B2 | 5/2005 | Jameel et al. | |
| 7,047,204 B1 * | 5/2006 | Wood et al. | 705/4 |
| 7,078,647 B2 | 7/2006 | Kou et al. | |
| 7,239,285 B2 | 7/2007 | Cook | |
| 7,280,988 B2 | 10/2007 | Helsper et al. | |
| 7,424,437 B2 | 9/2008 | Maus et al. | |
| 7,668,734 B2 * | 2/2010 | Pugh | 705/2 |
| 7,742,982 B2 * | 6/2010 | Chaudhuri et al. | 705/38 |
| 2006/0206724 A1 * | 9/2006 | Schaufele et al. | 713/186 |
| 2007/0061169 A1 * | 3/2007 | Lorsch | 705/3 |
| 2007/0075135 A1 * | 4/2007 | Dettinger et al. | 235/382.5 |
| 2008/0109370 A1 * | 5/2008 | Moshir et al. | 705/64 |

OTHER PUBLICATIONS

"Information Aggregation and Group Decisions", Sobel, University of California, San Diego; Jan. 17, 2006; Journal of Economics Literature.

* cited by examiner

*Primary Examiner* — Jason Lee
(74) *Attorney, Agent, or Firm* — Carl M. Napolitano; GrayRobinson, P.A.

(57) ABSTRACT

A computer implemented system and method verify and validate a user identity for enrollment in a secure personal dataset accessing system. A personal dataset includes identifiable attributes of the user. Using a computer, authenticity of an asserted user identity includes electronically verified identifiable attributes to form the personal dataset. A biometric identifier of the user is automatically captured for validating the identifiable attributes by confirming that the asserted identity matches the identifiable attributes. A traceable e-audit trail is provided in an enterprise infrastructure and bench mark performance indicator. A digital security element is generated and results in the user electronically receiving a password and a unique electronic address is assigned to the user. The digital security element is then transmitted to the user from the computer and enables electronic access to the personal dataset relating to the user, the personal dataset having been authenticated through the verification and validation.

27 Claims, 17 Drawing Sheets

FIG. 4A

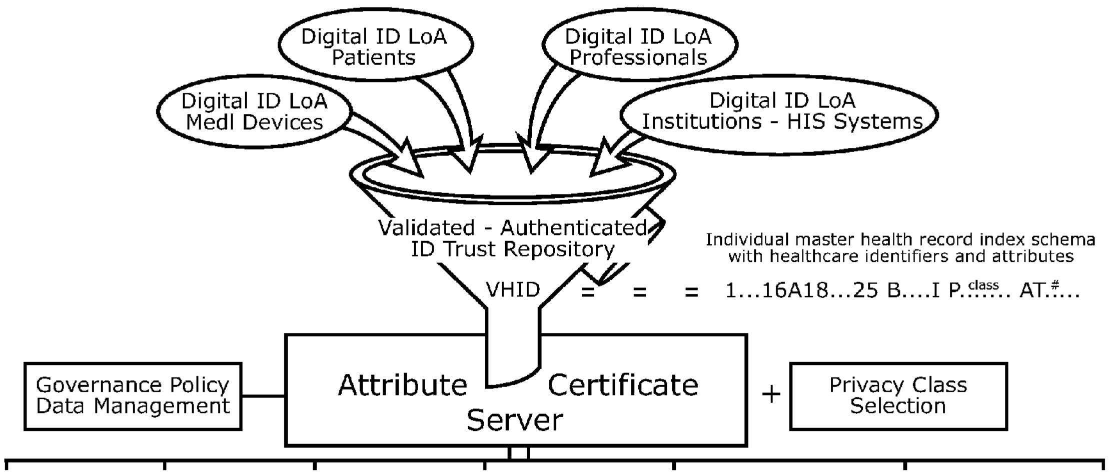

| Attribute Entity Classes | | Healthcare Actors IDs Roles Subjects | Hospitals IDS Institutions - Health Systems (Objects) | Docs & Security Access Control generated by Patient | Health data Received from: (My Repositories) | Health Insure Exchange Commnity Service Network Corp's Foundations Businesses | Medical Device Tech & Images & Interface Engine w/Attributes | Health-data tech tools apps programs w/Attributes |
|---|---|---|---|---|---|---|---|---|
| | | 1 | 2 | 3 | 4 | 5 | 6 | 7 |
| **Attribute Base Names & Functions** *each entity line item has a unique attribute # for access control* | A | Me / Patient Admin-Staff-Profess | Hospitals-Clinics Radiology | Consents MS's Nurses ED | ref: Self-Personal Caregiver | ER Data Set or Secure Repository | IPads PC's Tablets Cell phone UDIs | Patient Portal Trusted Attributes & P classes |
| | B | Physicians EMT's | HIS-Clinical Insur EOB 270-271 | ID-Role Privileges ER Medical Data Set | Physicians Nurses EHR EMR PHR | Federal-State-Community Databases | Tel Medicine & TV Technology | Financial - WEDI Transactions |
| | C | Nurses + Care Coordinator | Med - Offices & Facilities | Directives - DNA Organ donation | Hospitals Clinics PBM HISP's | MD's Hospitals Clinics Insurers NLETS | Remote User Secure Access | Medical Edu Material + Patient Sat Survey |
| | D | Therapists Pharmicist | ACO PCMH Med-networks | Break-the-Glass ER Access Mode | Rxs Labs Patho Radiology-Images | Clinical Trials PI-Research | Digital & e-Sigs e-Notorization | Risk MGT Assurance & Analysis - Data Storage |
| | E | Labs Radiology Pathology | Payers TPA's Medical Banking | Blood, Tissue & Gene Banks | Insuran Claims Data 835 & 837 | Certified Exchanges HISP Secure Message | Health data storage devices | Compliance Audits w/ real time acc. logs |
| | F | Power-of-Attorney Phycologist | Social Service & Health clubs | Family Friend Guardian | Blood Donation Nurse Coordinator | Care Plans Workmans Comp H Assesment Tools | Remote Medical monitoring devices | CPOE & Evidence Based guidelines |
| | G | Guardian Legal Agent Health Coach | EMT Ambulance AirVac FEMA Med Specialty | Power of Attorney my Will Social Worker | Blue Button + data Emergency Contacts Health Coach | Outcomes & Analysis Clinical Attribute - Value Sets | Medical Device Certification App Audit | Clinical Decision Support Care Plan Med-reconciliation |
| | H | Employee HR dept Financial Rep Pat & Provider errors | Pharmacy's Labs Therapy centers System Errors | Faith Based rep. Med Counselors 3rd party Rep | Cancer Heart Vaccine reposit Attribute Values | Rehabilitation Center Long Term Care facilities Home Healthcare | Risk Analysis & FDA Compliance RFID QR Barcodes | Patient Incentives w Documentation $ or % Discounts |
| | I | Health Advocate Principal Investigate | Chronic Disease health specialists | Self-track my health Dodument my vitals | YMCA & GYMs Specialty Health Clubs | Accum Chronic Dis Rela Data Capture | Subdermal Chip Real-Time Location System | Relational P-data compare searches |

FIG. 5A

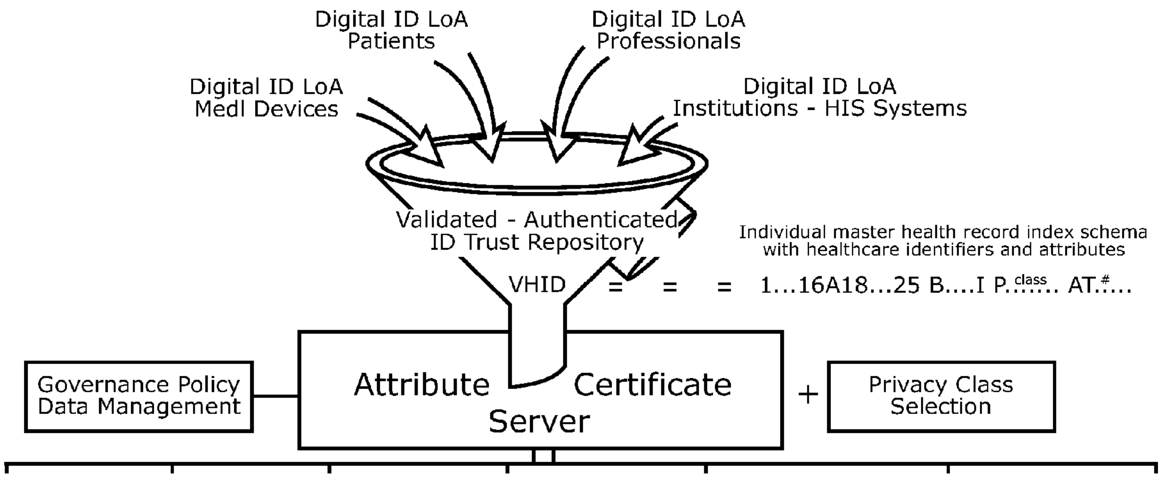

| Attribute Entity Classes | | Healthcare Actors IDs Roles Subjects | Hospitals IDS Institutions - Health Systems (Objects) | Docs & Security Access Control generated by Patient | Health data Received from: (My Repositories) | Health Insure Exchange Commnity Service Network Corp's Fondations Businesses | Medical Device Tech & Images & Interface Engine w/Attributes | Health-data tech tools apps programs w/Attributes |
|---|---|---|---|---|---|---|---|---|
| | | 1 | 2 | 3 | 4 | 5 | 6 | 7 |
| **Attribute Base Names & Fuctions** *each entity line item has a unique attribute # for access control* | A | Consumer/Patient Admin-Staff-Profess | Hospitals-Clinics Radiology | Consents MD's Nurses ED | ref: Self-Personal Caregiver | Community Service Centers Blood & Food Banks | iPads PC's Tablets Cell phone UDIs | Patient Portal Trusted Attributes & P classes |
| | B | Physicians EMT's | HIS-Clinical Insur EOB 270-271 | ID-Role Privileges ER Medical Data Set | Physicians Nurses EHR EMR PHR | Fed-State-Local PH databases Specialty Medical Clinics | Tel Medicine & TV Technology | Financial - WEDI Transactions |
| | C | Nurses + Care Coordinator | Med - Offices & Facilities | Directives - DNR Organ donation | Hospitals Clinics PBM HISP's | Hospitals & Pub H Clinics Corrections | Remote User Secure Access | Medical Edu Material + Patient Sat Survey |
| | D | Therapists Pharmacist | ACO PCMH Med-networks | Break-the-glass ER Access Mode | Rxs Labs Patho Radiology Images | Soc Shelters-Salvation Army Occupational Health-Environment | Digital & e-Sigs e-Notorization | Risk Mgt Assurance & Analysis - Data Storage |
| | E | Labs Radiology Pathology | Payers TPA's Medical Banking | Blood, Tissue & Gene Banks | Insuran Claims Data 835 & 837 | Non-Profit Service Groups Communtiy Foundation | Health data storage devices | Compliance Audits w/ real time acc. logs |
| | F | Power-of-Attorney Phycologist | Social Service & Health clubs | Family Friend Guardian | Blood Donation Nurse Coordinator | Chamber of Commerce Corporations - Businesses | Remote Medical monitoring devices | CPDE & Evidence Based guidelines |
| | G | Guardian Legal Agent Health Coach | EMT Ambulance AirVac FEMA Med Specialty | Power of Attorney my Will Social Worker | Blue Button + data Emergency Contacts Health Coach | State- Local Agencies Profess, Licensing & Registrations Admin staff & registered Agents | Medical Device Certification App Audit | Clinical Decision Support Care Plan Med-reconcillation |
| | H | Employee HR dept Financial Rep Pat & Provider errors | Pharmacy's Labs Therapy centers System Errors | Faith Based rep. Med Counselors 3rd party Rep | Cancer Heart Vaccine reposit. Attribute Values | Rehabilitation Center Long Term Care facilities Home Healthcare | Risk Analysis & FDA Compliance RFID qR Barcodes | Patient Incentives w Documentation $ of % Discounts |
| | I | Health Advocate Principal Investigate | Chronic Disease health specialists | Self-track my health Document my vitals | YMCA & GYMs Specialty Health Clubs | Accum Chronic Dis Rela Data Capture | Subdermal Chip Real-Time Location System | Relational P-data compare searches |

FIG. 6

PVID
Privacy
Class
Matrix

| **Privacy Levels** | **Class Name** | Temporary | Test | General | Psychiatry | Cancer | HIV | Research | Genetics | Organ Registry | Transplant History | Employer | HIE Participation | Authorizations | | | | | | | | | | Privacy Security Access/Class Definitions |
|---|---|---|---|---|---|---|---|---|---|---|---|---|---|---|---|---|---|---|---|---|---|---|---|---|
| Share all Data | | | | | | | | | | | | | | | | | | | | | | | | |
| Restricted data sharing | | | | | | | | | | | | | | | | | | | | | | | | |
| Sharing with restricted access | | | | | | | | | | | | | | | | | | | | | | | | |
| No sharing of data | | | | | | | | | | | | | | | | | | | | | | | | |
| Emergency Only | | | | | | | | | | | | | | | | | | | | | | | | |
| Consents | | | | | | | | | | | | | | | | | | | | | | | | |
| Preferences Authorizations | | | | | | | | | | | | | | | | | | | | | | | | |
| Directives DNR, organ donation | | | | | | | | | | | | | | | | | | | | | | | | |
| Opt-in - Opt-out | | | | | | | | | | | | | | | | | | | | | | | | |
| Medical - Power of Attorney | | | | | | | | | | | | | | | | | | | | | | | | |

| ATTRIBUTE GROUPS | | Legal Name with limited demographic data | Opt-Out No data sharing except column-e# A1 | Share Emergency Medical & Contact Data | Opt in share my PHI with Medical Network | Understand PHI will be e-encrypted & shared via HIE's | Will use the following devices to create-share-receive PHI | Attribute aggration function |
|---|---|---|---|---|---|---|---|---|
| FUNCTION | | A | B | C | D | E | F | G |
| Consent | 1 | Y (default) | Y N | Y N | Y N | Y N | Personal Computer | |
| | 2 | | | | | | Tablet | I understand attributes can be bundled to enhance efficiencies in sharing and distributing my Protected Health Information |
| | 3 | | | Break the Glass | | | iPad | |
| Understand | 4 | | | Y N | | | SmartPhone | |
| | 5 | | | | | | cell phone | |
| Restricted Data Sharing | 6 | | | Y N | Y N | | medical device(s) | |
| | 7 | | | | | | other mobile devices | |
| Restricted Access | 8 | | | Y N | Y N | | I consent that the selected device(s) will be used by me in manageing my health activities or by an entrusted 3rd party with a digital ID and LoA equal to or greater than mine. | ☐ I agree |
| | 9 | | | | | | | |
| Sharing with Restricted Access | 10 | | | | Y N | | | |
| | 11 | | | | | | | |
| | 12 | | | | | | | |
| | 13 | | | | | | | |
| | 14 | | | | | | | |
| | 15 | | | | | | | |
| | 16 | | | | | | | |
| Consent | 17 | | | | | | Y N | |

MY PHI DATA
Segmented e-records

Hospitals ACO's PCMHs
Home healthcare
Rehab Centers Nursing HOMES
PHI Analytics
Genetics
HIV
STD
Cancer
Psychiatry
Research
e Health Record
Private medical tests
Juvenile Abuse - age issues
Adult Abuse
Workmans's Comp
HR Department Workplace
Profile change
Attibute Change
Authentication Change
Child/children health records
Clinical value sets
Chronic Disease event records
e-Audit Trails
Care Plan Mgt
My Health Data Repository
Date - Time clock
Banks: Gene, Egg, tissue, Sperm, Blood, etc
New VHID#
Temporary VHID#
Anonymous Temp VHID#
End of Life Care
Mobile-Medical Device Images
PHI Errors and Recovery Res and Professional Approved & Authenicated with Digital ID LoA 3cr

| Actors / Subjects | | A | B | C | D | E | F | G | H | I | J | K | L | M | N | O | P | Q | R | S | T | U | V | W | X | Y | Z | Ab | Ac | Ac | Ad | Ae | Af | Ag | Ah |
|---|---|---|---|---|---|---|---|---|---|---|---|---|---|---|---|---|---|---|---|---|---|---|---|---|---|---|---|---|---|---|---|---|---|---|---|
| Self-My PHI | 1 | | | | | | | | | | | | | | | | | | | | | | | | | | | | | | | | | | |
| Family Friend | 2 | | | | | | | | | | | | | | | | | | | | | | | | | | | | | | | | | | |
| Caregiver Gardian | 3 | | | | | | | | | | | | | | | | | | | | | | | | | | | | | | | | | | |
| Physician General - Specialist | 4 | | | | | | | | | | | | | | | | | | | | | | | | | | | | | | | | | | |
| Caregiver Gardian | 5 | | | | | | | | | | | | | | | | | | | | | | | | | | | | | | | | | | |
| Nurses EMT | 6 | | | | | | | | | | | | | | | | | | | | | | | | | | | | | | | | | | |
| Pharmacist | 7 | | | | | | | | | | | | | | | | | | | | | | | | | | | | | | | | | | |
| Radiology Therapist | 8 | | | | | | | | | | | | | | | | | | | | | | | | | | | | | | | | | | |
| Psysiologist Psychologist | 9 | | | | | | | | | | | | | | | | | | | | | | | | | | | | | | | | | | |
| Health Coach Health Advocate | 10 | | | | | | | | | | | | | | | | | | | | | | | | | | | | | | | | | | |
| Financial Rep Claims data rep | 11 | | | | | | | | | | | | | | | | | | | | | | | | | | | | | | | | | | |
| Principal Investigator Auditor | 12 | | | | | | | | | | | | | | | | | | | | | | | | | | | | | | | | | | |
| 3rd Part Claims Rep Risk Analysis Professional | 13 | | | | | | | | | | | | | | | | | | | | | | | | | | | | | | | | | | |
| Agent Trustee Medical Power of Attorney | 14 | | | | | | | | | | | | | | | | | | | | | | | | | | | | | | | | | | |
| Chronic Disease Specialist Health Educator | 15 | | | | | | | | | | | | | | | | | | | | | | | | | | | | | | | | | | |
| Spiritual Representative Anonymous Trustee | 16 | | | | | | | | | | | | | | | | | | | | | | | | | | | | | | | | | | |
| Workmans Comp | 17 | | | | | | | | | | | | | | | | | | | | | | | | | | | | | | | | | | |
| My VHID # Stolen, Compromised, or Breached. Need new VHID# | 18 | | | | | | | | | | | | | | | | | | | | | | | | | | | | | | | | | | |
| Create a Temporary VHID # | 19 | | | | | | | | | | | | | | | | | | | | | | | | | | | | | | | | | | |
| Create an Anonymous VHID # | 20 | | | | | | | | | | | | | | | | | | | | | | | | | | | | | | | | | | |
| Patient and Provider errors | 21 | | | | | | | | | | | | | | | | | | | | | | | | | | | | | | | | | | |

Emergency Medical Data Set* *for*

Name: Octivia Helios Gender: Female EMPI: NA

Authenticated* Primary HIE/RHIO: Orlando, FL FLCF32802-115

Confidential

Personal Data - Contact Information

DOB: January 22, 1945
Race/Ethnicity: Hispanic American
Primary Language: Spanish
Home Address: 123 Bastile Dr. Apt. 3
Boston, MA 02102
Phone number: home 999-999-9999
cell: 111 111-1111

Emergency Contact Data:
Physician contacts:
Dr. Thomas E. Duitrite - Primary Care
office # 999-999-9999
Dr. Julie P. Quantos OBGYN
office # 999-999-9999
Family/Friend contacts:
Hector Helios Husband 111-111-1111
Juanita Rodrigus Friend 111-111-1111

Dependent family members under 18:
Juan Hulios-son 17 - chronic;
Sally Helios-daughter - 15 w/disability
Billy Ann Helios-son - 9
Juanita Helios-daughter - 3

Local ER or Trauma Center:
Name Santa Clara General Hospital
Phone# 888-888-8888

Driver License # 7221-449-331AX
State: Florida
Vehicles registered in: Georgia
Vehicle #1 License Plate # 887 AB7A
VIN # A227 9999 3333 2222 - ACA
Vehicle #2 License Plate # 257 476B
VIN # TRC3 7777 9999 8888 1111

Insurance Coverage:
Blue Cross Blue Shield of California
Plan Name: Options for Good Blue Health
Policy# XRGH12131456577
Group# BA11398
Contact# 1-877 999-1234

*Individual voluntarily consented to an Opt-in
Preference to share this Emergency Medical Data generated from their Personal Health Record on 04/25/2009 11:11PM PDT

Emergency Medical Data

*BLOOD TYPE:* AB+

*ALLERGIES:* *as of 12/03/2009*
*Latex - severe*
*Sulfa - severe*
*Peanuts - mild*
*Feline Dander -moderate*

*PROBLEM LIST* *as of 3/11/2009*
*Hemoptysis,*
*Mitral Valve Replacement,*
*Congenital Subaortic Membrane,*
*Chronic Atrial Fibrillation,*
*Diabetes Mellitus Type 2,*
*Stroke without residual deficit,*
*Congestive Heart Failure, Sciatia*

*Active MEDICATIONS* *as of 3/11/2009*
*Spironolactone (Aldactone),*
*Amoxicillin (Amoxicillin),*
*Warfarin (Coumadin),*
*Digoxin (Digitek),*
*Valsartan (Diovan),*
*Ferous gluconate (Ferrous Gluconate),*
*GlyBURIDE (GlyBURIDE),*
*Furosemide (Lasix),*
*Metformin (Metformin Hydrochloride),*
*Acetaminophenhydrocodone (Vicodin)*

*ADVANCE DIRECTIVES* *as of 4/25/2009*
*DNR and Living Will on file at Attorney's office*
*Medical Surrogate is named Hector Helios*
*Organ donation directive on file at State* james amigo
Digitally signed by james amigo
DN: cn=james amigo, o=TNT, ou=223, email=goto@home, c=US
Date: 2010.02.01 07:53:17-05'00'

Confidential - Emergency Medical Data and Contact Information - Confidential

Copyright Good Health Network, Inc. 2009

FIG. 8

Emergency Contact and Medical Consent Data* *for*

Name: Octivia Helios Gender: Female EMPI: NA
Authenticated* Primary HIE/RHIO: Orlando, FL FLCF32802-115
Confidential

Emergency Contact Data

DOB: January 22, 1945
Race/Ethnicity: Hispanic American
Primary Language: Spanish
Home Address: 123 Bastile Dr. Apt. 3
Boston, MA 02102
Phone number: home 999-999-9999
cell: 111 111-1111

Emergency Contact Data:
Physician contacts:
Dr. Thomas E. Duitrite - Primary Care
office # 999-999-9999
Dr. Julie P. Quantos OBGYN
office # 999-999-9999
Family/Friend contacts:
Hector Helios Husband 111-111-1111
Juanita Rodrigus Friend 111-111-1111

Dependent family members under 18:
Juan Hulios-son 17 - chronic;
Sally Helios-daughter - 15 w/disability
Billy Ann Helios-son - 9
Juanita Helios-daughter - 3

Local ER or Trauma Center:
Name Santa Clara General Hospital
Phone# 888-888-8888

Health Insurance Data:
Blue Cross Blue Shield of California
Plan Name: Options for Good Blue Health
Policy# XRBH12131456577
Group# BA11398
Contact# 1-877-999-1234

Law Enforcement Emergency Contact Data
Driver License# 7221-449-331AX
State: Florida
Vehicles registered in: Georgia
Vehicle #1 License Plate # 887 AB7A
VIN # A227 9999 3333 2222-ACA
Vehicle #2 License Plate # 257 476B
VIN # TRC. 7777 9999 8888 1111

*Individual voluntarily consented to an Opt-in
Preference to share this Emergency Medical Data generated from their Personal Health Record on 04/25/2009 11:11PM PDT

Emergency Medical Data Available For Licensed Medical Providers

EMT / ED Physicians / Trauma Centers Can Access Emergency Medical Data at Emergency Repository

Digitally signed by Michael Jahn
DN: cn=Michael Jahn, o=Jahn & Associates, ou=Management, email=michaelejahn@gmail.com, c=US
Date: 2009.12.09 12:46:36-08'00'

Confidential - Emergency Medical Data and Contact Information - Confidential
Copyright Good Health Network, Inc. 2009

FIG. 9

Personal Health Record   Lite

Site Map | Help | Audit | Log Off

| Personal | Medical | History | Tracking | Summary |

John Smith

Member Number: 35669495575     00/00/0000

| Emergency Data | Personal Summary | Continuity of Care Record |

⊕     Ⓟ     CCR

This is a summary for critical health information

This summary has more detailed information added to your emergency summary.

This the most complete summary that is generated from your Journal

[View] [Print] [eMail]     [View] [Print] [eMail]     [View] [Print] [eMail]

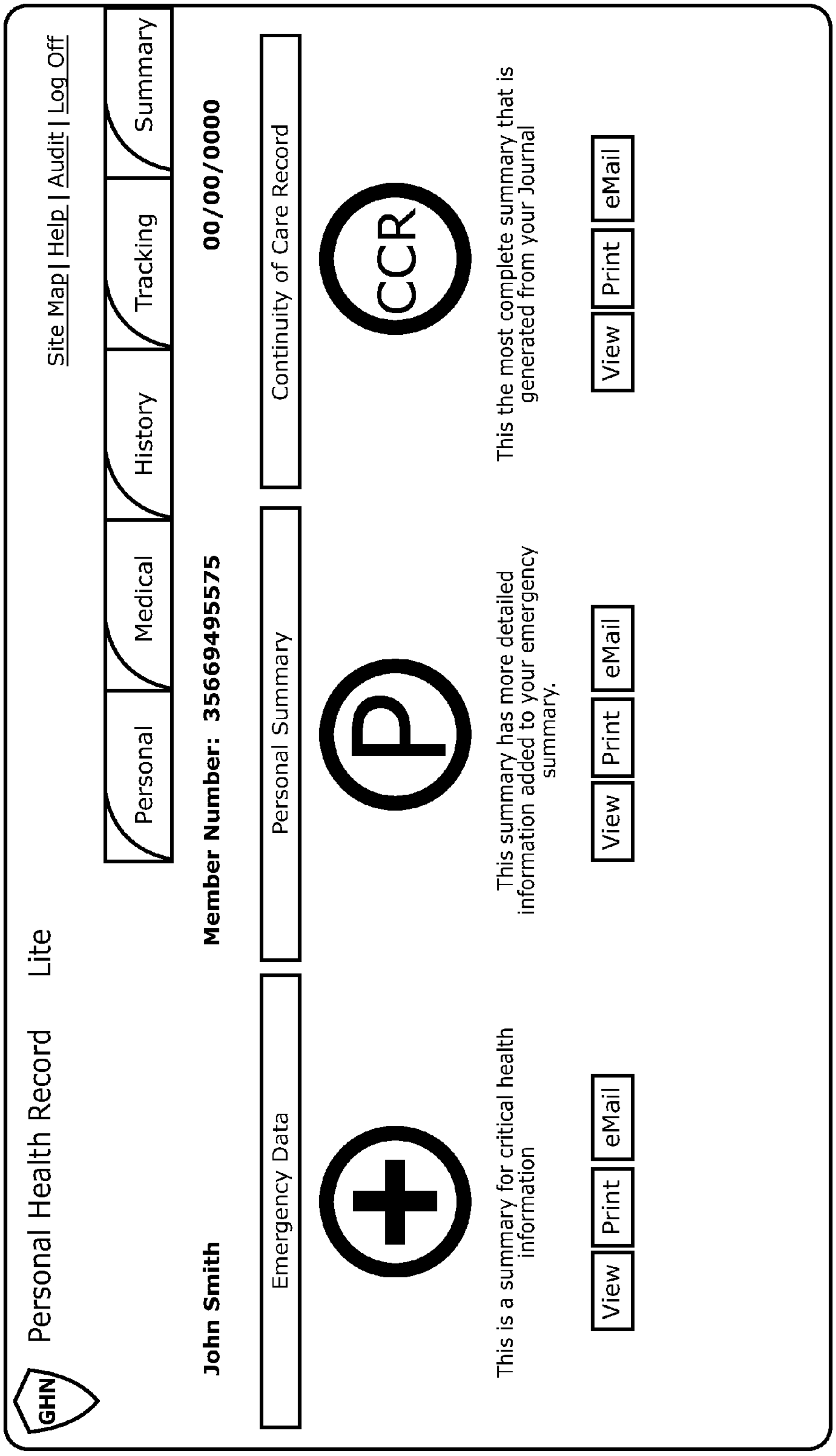

FIG. 10

IDENTITY VALIDATION AND VERIFICATION SYSTEM AND ASSOCIATED METHODS

CROSS-REFERENCE TO RELATED APPLICATIONS

This application is a Continuation-In-Part application of and claims the benefit of pending U.S. Utility application Ser. No. 12/792,980, filed Jun. 3, 2010, which itself claims priority to Provisional Patent Application Ser. No. 61/183,600, filed Jun. 3, 2009, the disclosures of which are herein incorporated by reference in their entirety, and commonly owned.

FIELD OF THE INVENTION

The present invention relates to secure data access systems, and more particularly, to such data access systems that operate under emergency conditions such as needed in medical service environments.

BACKGROUND OF THE INVENTION

The Health Insurance Portability and Accountability Act of 1996 (HIPAA), the fundamental privacy principles of both the Data Protection Act and the Human Rights Act 1998, and the American Recovery and Reinvestment Act (ARRA) in February 2009 followed by April rulings by the Federal Trade Commission (FTC) included a standard of privacy regarding an individual's right to privacy regarding health care data. In January 2013, a new revision of HIPAA 1996, labeled the HIPAA omnibus rule, was issued with increased emphasis on privacy, disclosure of identifiable information and tougher security provisions which comes under the 2009 HITECH Act and the Genetic Information Nondiscrimination act. Under the provisions of HIPAA, ARRA, and the FTC, health information, with few exceptions, can only be shared with the express permission, advance consent, and authorization of the patient (or the patient's legal guardian, as appropriate), and when compromised, electronic notifications must be sent, and followed up with electronic audits and risk analysis.

By way of example, if a patient is unconscious and has provided advance authorization and consent for a licensed health care provider to securely access and view health-related and protected health information with family, next-of-kin, friends, or others involved, the patient's care and emergency care can be shared when in the best interest of the patient.

In Florida, vehicle owners can securely store emergency contact information electronically, including the name and telephone number of at least one person, and link same to their driver's licenses (DL). A law enforcement officer or first responder, if they can locate a driver's license at an accident scene, can contact the Department of Motor Vehicles to obtain emergency contact (ER-Cont) data. If not available and the vehicle occupants are unconscious or otherwise unable to communicate, notifying the family can be a challenge. ER-Cont information is only available to police at a crash scene in the state of Florida.

NLETS, the National Law Enforcement Telecommunications System, can interface with Department of Motor Vehicle sites across the country and obtain emergency contact information, but only if linked to a vehicle's vehicle identification number (VIN) and with the driver's consent. However, medical data cannot be collected, stored, accessed, or shared via NLETS, which can cause a loss of critical time gaining access to critical healthcare data, such as allergies, blood type, and other medical data. Such data can save lives or improve the quality of life after a life-threatening event.

As will be addressed throughout this disclosure, attributes contain information about a subject (known also as an actor). A subject's digital ID has a limited number of identity attributes such as address, age, title or driver's license or trait features that are inherent such as eye color, gender or birth place. A subject can also have acquired associated attributes (lifestyle, purchasing behavior, medical or banking activities) which can change easily whereas trait attributes most likely do not change. Upon being validated and authenticated with a digital ID (public key certificate) in good standing, then a person's (subject) authenticated identity can be enhanced with attributes that originate from an Attribute Certification process where one's Authentication privilege is extended to provide "certified binding attributes' such as access control, secure email, access privileges and associated relationships. As a result of the security and auditing process incorporated into Attribute Certification there is a strong privilege management policy monitoring effort, risk management process and certificate revocation process. Entities, institutions, exchanges, enterprise servers and the environment (defined as 'objects') can also have attributes which are represented by defined characteristics and functions. Attribute certs cannot be used to establish an identity but are used to extend the attributes of one's identity. The forgoing is in concert with NIST guidelines.

Anonymization and Pseudonymization are specific de-identification processes that file the intent of HIPAA 1996 and the HIPAA omnibus rules of January 2013. Anonymization is the process that removes the identifying characteristics (HIPAA defined) associated with protected health/clinical information and generates a not so unique health data set. The value of such allows a subject/patient to make a part of or subset of their clinical data available for a range of secondary purposes without having to access identifiable clinical information. Such data will be made available on a need to know or on an arranged basis and risk of identity is greatly minimized. The activity is handled through a trusted third party who attests to the validity of the clinical information. Pseudonymization is a specialized class of Anonymization that removes the association and adds an association between a particular set of data characteristics relating to the data subject in addition to adding more pseudonyms. This is a means by which information can be linked together to the same group of persons over time and across multiple data records without revealing the identity of the person and subject data. A trusted third party play's a critical role if there needs to be a re-identification event that is in response to a major public health event. (Activities defined in HIPAA and HITSP).

Therefore, it would be beneficial to provide a secure system and method for making both VIN and emergency medical data available on an as-needed basis to licensed emergency medical responders, in order that care be provided in a more efficient, safe, and secure fashion if such data can be voluntarily provided and stored in a secure and separate, non-law-enforcement repository, and linked to the NLETS secure infrastructure.

SUMMARY OF THE INVENTION

A system and method are provided for establishing and administering an online secure data sharing network, in particular, for use in emergency situations wherein a patient is unconscious or otherwise unable to communicate. The network enables first responders to identify victims, reach next-of-kin, reach their medical doctor, and access emergency medical data at a crash scene or other life-threatening event, the emergency data having previously been authorized for access by the patient.

The network includes an emergency medical data registry for each person who elects to participate, by validating, authenticating their identity, and consenting to securely provide emergency medical data on themselves and, if applicable, their children. Such emergency medical data can include, for example, blood type, allergies, current medications, surgeries, and emergency medical contact information. The emergency medical data can only be presented in a standards-based format and viewed by a licensed healthcare worker, such as an emergency medical technician (EMT) or emergency department staff member. The data are owned by the participant, and can only be modified or deleted by that person. A real-time audit trail is available to the participant, documenting all access events, and a qualified and licensed security professional must be able to access a specific emergency event audit trail for independent auditing purposes without having access to or the ability to view any protected health data.

Embodiments of the invention may comprise a computer implemented system or method to verify and validate a user identity for enrollment in a secure personal dataset accessing system, wherein a personal dataset is electronically received and includes identifiable attributes of the user. Using a computer, authenticity of an asserted identity of the user including the identifiable attributes is electronically verified and a personal dataset formed. A biometric identifier of the user is automatically captured on the computer for validating the identifiable attributes. The validating includes confirming that the asserted identity matches the identifiable attributes. An e-audit trail is provided having a traceable electronic enterprise infrastructure and bench mark performance indicator. A digital security element is generated as a result of the verifying and validating process and results in the user electronically receiving a password, wherein a unique electronic address is assigned to the user. The digital security element is then transmitted to the user from the computer and enables electronic access to the personal dataset relating to the user, the personal dataset having been authenticated through the verifying and validating steps.

A system and method for adding participants and licensed professionals to the network is an important feature of the present invention, and will be discussed in detail in the following.

Another registry is established for licensed emergency healthcare providers and institutions, so that their credentials, qualifications, and access privileges can be independently verified real time via a third-party source (policy and procedures) and that such validation will enable them to access the emergency medical data registry at local, regional, or national emergency events. Among the healthcare workers and institutions who may enroll are EMTs, physicians, nurses, hospitals, trauma centers, and ambulance, EVAC and AIRVAC networks, although these are not intended as limitations.

BRIEF DESCRIPTION OF THE DRAWINGS

Embodiments of the invention are described by way of example with reference to the accompanying drawings in which:

FIG. 4A is an Attribute functional matrix for one line item Role Based Access Control and Privacy Class data management illustrating a patient ID and relational entity attribute structure with designated functions for access control, by way of example;

FIG. 5A illustrates one digital object ID with relational attribute structure and designated privacy and access control functions for a "health-e-community," by way of example, with a focus on registered third party entities, enterprise, organizations, human resource departments, health information service provider (H ISP), identity providers, relying parties, defined repositories, associations, clubs to include government agencies, insurers, institutions and trusted authorities;

FIG. 6 is an exemplary privacy class matrix, expanded into three relational entity attribute processes;

FIG. 6A illustrates health system infrastructure interfaces (e.g. "objects") such as infrastructure, transport, HIE, HISP, and data capture mobile devices and tools, by way of example;

FIG. 6C illustrates names actor(s)/professional titles that can view defined PHI and shared with whom for a period of time, and a PHI that cannot be viewed, wherein a privacy control matrix is illustrated that designates attributes to a representative such as a medical professional, researcher, administrative specialist for an approved attribute entity, and wherein the designated representative is prequalified (having trusted credentials) to view and access a patient's protected health information as part of the healthcare management team;

FIG. 8 is an exemplary emergency medical data set according to the teachings of the present invention digitally signed by someone with access to the entire record, by way of example;

FIG. 9 is a portion of the data set (contact information) of FIG. 8, with the emergency medical data set hidden from view; and FIG. 10 is an exemplary screen shot of an exemplary portal for generating data in a user's personal health record.

DETAILED DESCRIPTION OF THE EMBODIMENTS

Figure 1:
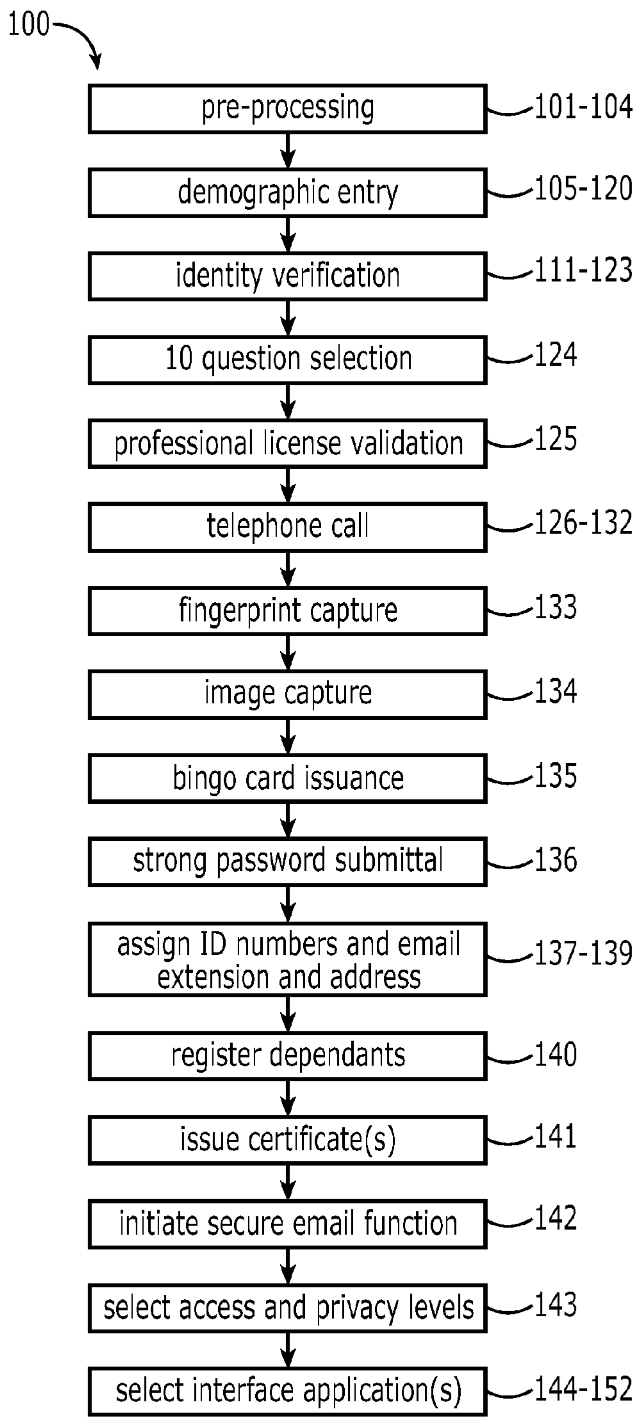
FIG. 1 is a flowchart of one process for identity verification and consent management according to the teachings of the present invention.
Figure 2A:
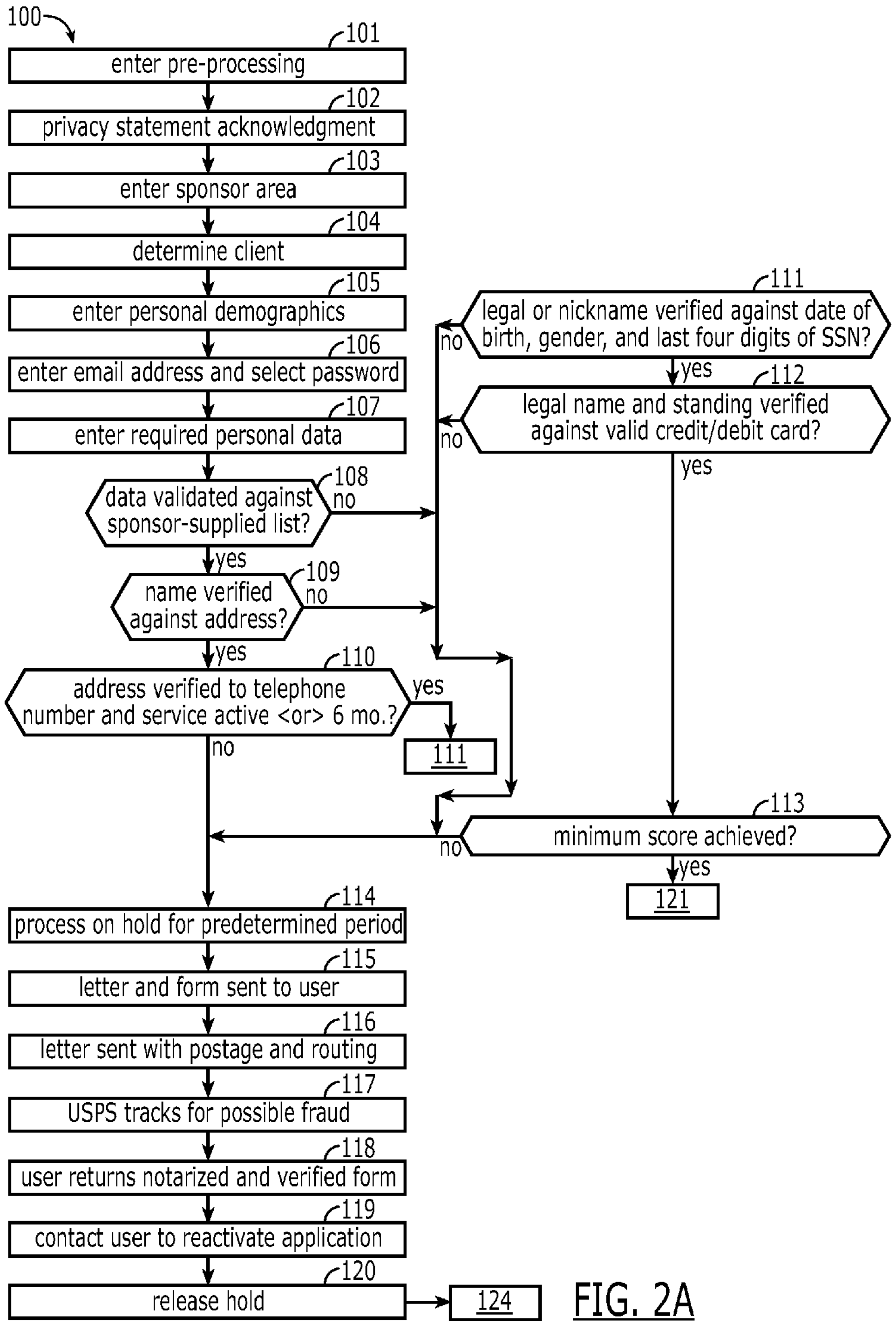
FIGS. 2A-2C are flowcharts having expanded details for the process and consent management system of FIG. 1.
Figure 2B:
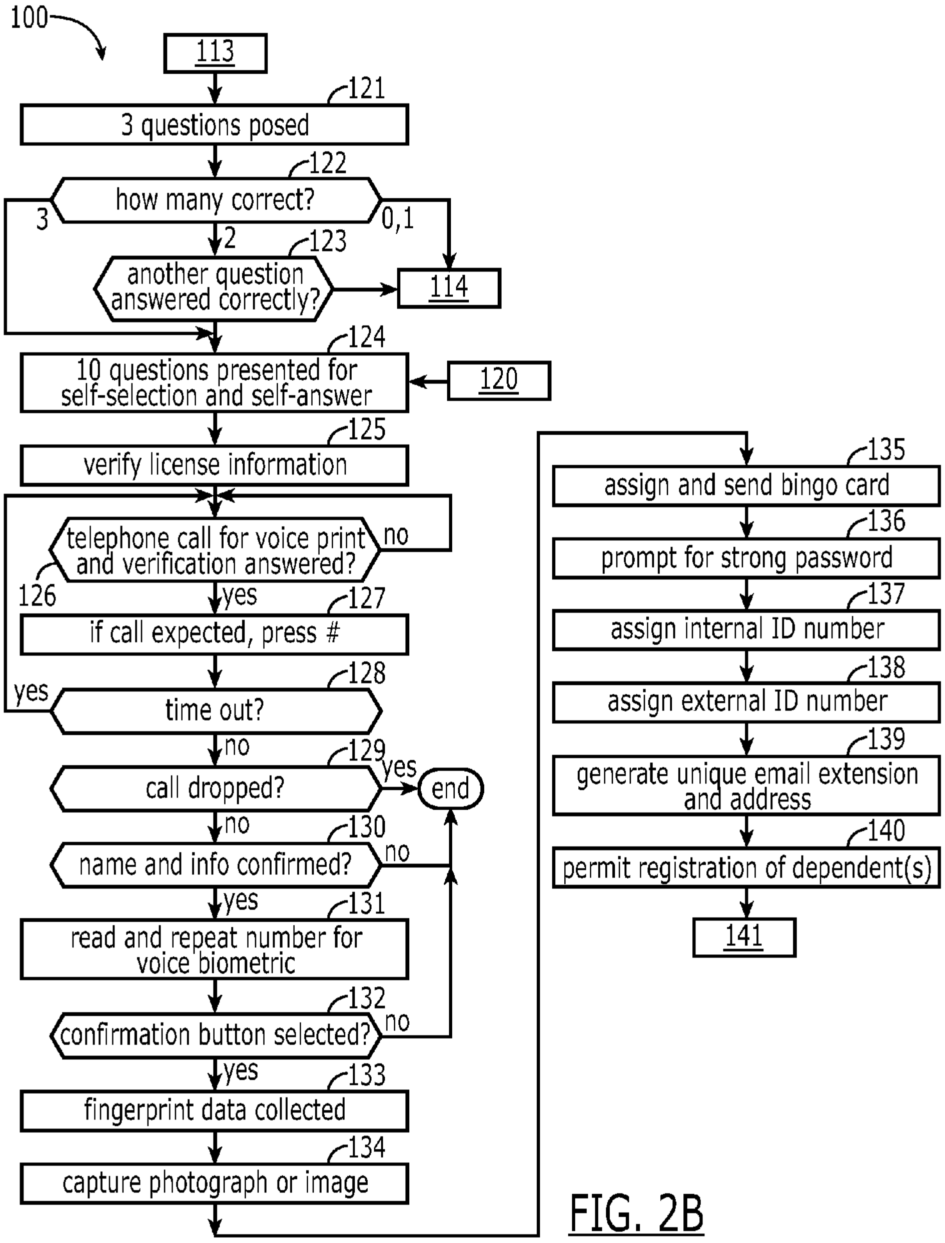
Figure 2C:
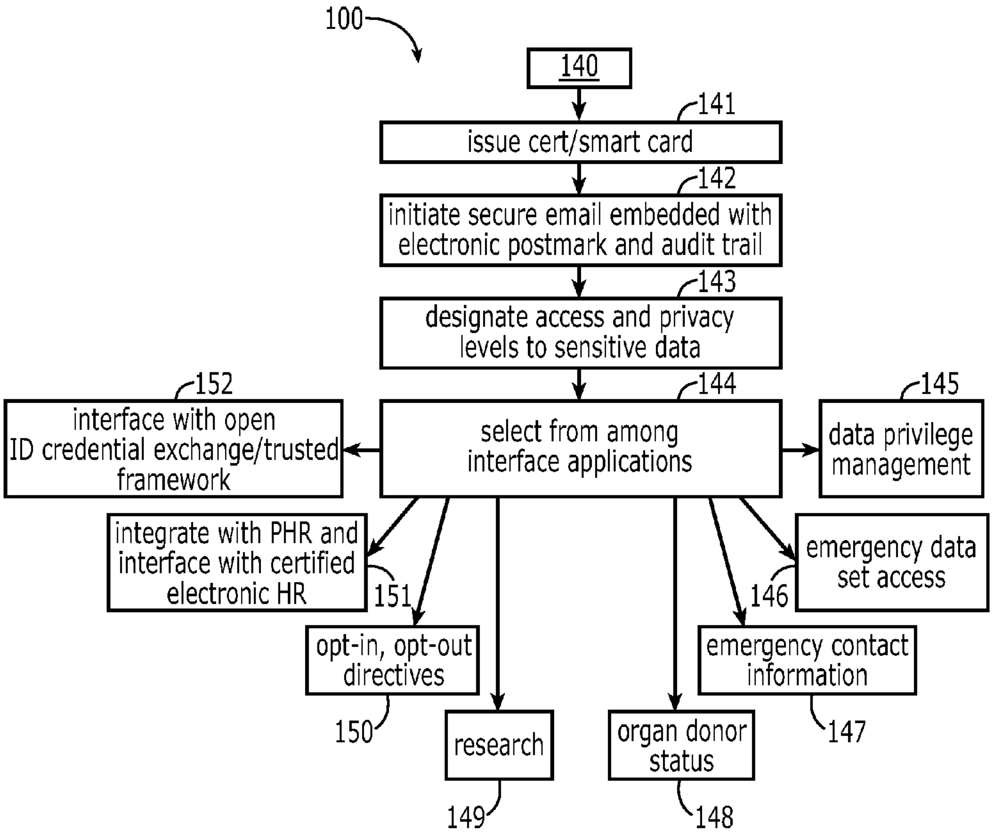

A description of embodiments will now be presented with reference to FIGS. 1A-10. An initial part of a process 100 for providing access to emergency healthcare data is directed to an enrollment process for the participant. The steps in this process 100 are outlined in the flowcharts of FIGS. 1-2C, with FIG. 1 comprising a high-level view and FIGS. 2A-2C, a more detailed view. Identity proofing is an important feature of the invention, which can have a plurality of levels depending upon the degree of assurance level desired. All levels preferably include validation of address and zip code (USPS).

A Level 1 assurance can comprise validation of a user name, with a possibly weak password being used. Level 2 can be attained with the use of a strong password and possibly a question or image definition. Assurance Level 3 requires a majority of the steps to be discussed in the following. The highest assurance level, LoA 4, would require all steps noted plus an FBI background check. There is escalating time and expense to advance through each level of assurance so in order to provide flexibility and adaptability the "Plus 1" function can be added (at any level of assurance) in order to reach a preselected level of assurance that needs to be achieved. By specifying the feature and then adding one additional (Plus 1) verifying requirement there can be an increased degree of assurance so different situations can be provided by an entity's being able to select a subset of the steps of the process 100 to achieve a desired level of assurance or to achieve a desired grade level for a given class of employee, customer or executive, for example. Therefore, the invention is not intended to be limited to the totality of the steps presented herein.

An exemplary multi-step identity verification and enrollment process 100 can include a preprocessing sector (block 101), which includes a user acknowledging receipt of a privacy statement acknowledgement (block 102).

The sponsor (block 103) can have, if desired, a customized front end web application for each client (block 104). Such a personalized web ID portal can include attributes by class, such as emergency data/directives; financial/educational; healthcare/Rx/trials; social clubs/associations; business/professional; family/e-coupons; personal/private/governmental; and mobile device registrations. One possible way of segregating the attributes is by presenting a plurality of, such as 20, pictures, from which the user selects and names one, and provides a hint word or phrase. This selection can be tested and accepted. When the next category is selected, the plurality of pictures, minus the previously selected one, is presented from which to choose.

The client can comprise, for example, an agency, association, corporation, organization, club, society, company, community, group, etc. The client may or may not provide a verifiable database of qualified persons as an initial match list used to control initial access and participant correlation.

Three general classifications of clients can comprise, but are not intended to be limited to, a consumer for family enrollment, which typically will not be vetted; a company desiring only basic demographic verification, which could use a third-party trusted site, their human resources department, a patient list, or an employee list, which typically will not be vetted; and a company that desires a fully vetted process, requiring a personal identifiable verification (PIV) card and corporate verification.

The substantive part of the process 100 begins with entry of demographic data (block 105), which can include entering an email address and a selected password (for verification reentry; block 106). All required personal data are also entered (block 107), which can include, but are not intended to be limited to, such as name, address, citizenship, social security number, etc.

A verification request screen provides the ability to perform further validation against sponsor supplied list (block 108). Acceptance may be recognized by elements such as a government-issued ID; driver's license, Medicaid, Medicare or Food Stamp card, a PIV card, a Green Card, or a passport with a magnetic stripe that can be swiped in a reader and electronically present a matching name. In addition, or in lieu of this, an employer, membership club or organization that issues magnetic stripe card can be used as a secondary validating source.

The verification process begins by verifying the user's name to his/her address (block 109), which can comprise a third-party verification of the entered street, and then verification of the user's name to the street. This step 109 can be performed, for example, by the U.S. Postal Service (USPS), although this is not intended as a limitation.

The user's entered address is also verified against the entered telephone number (block 110). If desired, an additional set of steps can comprise validating the user's first telephone number with their carrier, and, the telephone number has been active for less than 6 months, the number can be validated to an address, with the verification of the carrier.

Next the user's name is verified against the date of birth and gender along with the last four digits of the social security number (SSN; block 111), which will typically comprise a third-party verification.

The legal name of the user and his/her standing is also verified with a valid debit or credit card via a third party, such as a national financial institution (block 112). This will typically not entail a transaction, but rather the return of just a yes or no response of good standing.

Depending upon the assurance level requested, a positive acknowledgment from steps 108-112 must be met to a minimum value (block 113). Otherwise, the process is placed on hold for a predetermined period, for example, for up to 45 days (block 114). In this case, a letter and form are electronically sent to the user (block 115), who is asked to return the letter with postage and routing data (block 116). The carrier, for example, the USPS, tracks the letter for possible fraud (block 117), thereby providing third-party notarized verification.

The returned form letter will typically be required to be notarized, the credit/debit card verified, and mailed back to a designated address (block 118). When internally received, the form is date stamped and recorded. A message, such as an email, can be sent to the user, providing a personal access code to reactivate the application (block 119). The hold is then released "manually" (block 120) and the process 100 continues from block 124, joining those who had achieved the minimum score at block 113.

If the minimum score was achieved at block 113, three consumer-based questions are presented (block 121), such as, for example, third-party-providing knowledge-based questions. Depending upon the number of correct answers (block 122), the process 100 proceeds as follows.

If all three questions are answered correctly, the process continues at block 124. If only two questions are answered correctly, a fourth consumer-based question is posed (block 123), and, if this is answered correctly, the process proceeds to block 124. If either the fourth question is answered incorrectly, or only one of the three initial questions are answered correctly, the process 100 returns to block 114, wherein the process 100 is put on hold.

The process 100 for those who have satisfied the above conditions by presenting a plurality, for example, ten question options for self-selection and self-answer (block 124). The user's choices are captured and maintained.

Another aspect of the process 100 can include the verification of licensing information (block 125), such as those that the user may have acquired through training, schooling, and/or certification credits that can be issued nationally or in some other verifiable manner. Such licenses can include, but are not intended to be limited to, licenses to practice medicine, carry a fire arm, perform law enforcement duties, perform financial auditing services, carry out a professional trade, etc. These credentials can be validated, for example, via a recognized third-party credentialing service, and preferably will include an expiration date and certificate number.

A further aspect of the process 100 includes the placement of a telephone call for voice print and verification, which can comprise an out-of-bound third-party process (block 126). If there is no answer, the call can be repeated a predetermined number of times, for example, once. Preferably the user will have provided the telephone number to be used while the user is at a computer screen.

If the call is answered, the user is asked if the call was expected (block 127), in which case the user is asked to depress a telephone key, for example, the "#" symbol, to activate the telephone call part of the process. If the symbol is not pressed in a predetermined amount of time (block 128), the process ends, with a predetermined number, for example, one, repeat call, to be verified, allowable to the same telephone number. If the call is dropped (block 129), the process ends, and the user is requested to call the host, via, for example, a help desk.

If the call proceeds properly, the system repeats the user's name and confirms the entered data, and records the user's acknowledgement (block 130). Again, if there is no response, the process 100 ends. The user is asked to read and repeat the telephone number, in order to record a voice bio-metric (block 131). Then the user is asked to confirm that they provided the requested data by selecting a button (block 132). Again, if there is no response, the process 100 ends.

The process 100 continues by collecting the user's fingerprint information with the use of a third-party vendor, for example (block 133). The process 100 also includes the capture of the user's photograph and/or other type of image having a named definition (block 134). This could be provided, for example, by a third-party vendor.

The process 100 then proceeds by assigning a random "bingo card" to the user. The bingo card can be printed and transmitted to the user, for example, by a third-party vendor (block 135). As an example, a card having bar code functionality and RFID could be employed that interfaces with pre-approved authorized forms for consent management and privilege granting.

The user is prompted to devise a strong password for user authentication (block 136).

Next an internal unique identity number is generated and assigned (block 137) in concert with defined attributes and also a separate and distinct unique, external enterprise patient/consumer Voluntary Health ID controlled index number (VHID) is generated (block 138). The Internal role based and privacy attributes and external ID allows the consumer to manage and control privacy preferences, the sharing of restricted content such as protected health information, such as directives and emergency contact data. If a user elects to share a segment of their clinical health data for research or for the benefit of community health, they, through the anonymization function, de-identify their protected health information.

A unique email extension and address are generated (block 139) that function separately, for identity protection, and are separate and distinct from the current "user name," which is the email address used in the identity proofing process. This process can use an electronic post mark for emergency care patient tracking, incorporating the HITSP standard and using CCR and/or CCD record-tracking functions.

If desired, the user can identify and register dependents (block 140), such as minors, dependent seniors, or disabled persons under his/her full-time responsibility and direct care and who might, in an untimely accident, need to be identified and the care of whom would require access to their emergency data.

Once the user's identity has been validated via the foregoing steps, a digital certificate can be issued, for example, by a Certification Authority (block 141). Roaming certificates for fixed PC and mobile digital devices such as cell phones can be server-side based, and digital certificates, personal privacy and security attributes, can be integrated into smart ID cards in compliance with national NIST guidelines and FDA proposed regulations and HHS enterprise security and infrastructure exchange regulations.

To complete the substantive validation and registration process, a secure email function is initiated that is embedded with an electronic postmark and audit trail for secure data exchange (block 142). The trusted process validates the user's ID and provides an authentication process with electronic and digital signature functions (when using higher LoA's) and an e-audit function for non-repudiation. The process, which is preferably encrypted, focuses on access controls and privilege management using electronic marks integrated into each secure communication. This can apply, for example, to emergency data, a clinical trial, a financial transaction, secure document sharing, a "do not resuscitate" order (DNR), or a legal document exchange.

The user is permitted to designate levels of access to sensitive data, preferably in customized fashion (block 143). The user is asked to select a combination from among elements such as username and strong password plus one or more of the bingo card, a biometric ID, knowledge-based questions, the user's image, and digital signature, although these are not intended as limitations.

The user can also select from among at least the following interface applications (block 144) including: user preference relating to data privilege management (block 145), emergency data set access (block 146), emergency contact information (block 147), organ donor status (block 148), research (block 149), and opt-in and opt-out directives (block 150). The data can be integrated with a certified personal health record and interface with a certified electronic health record (block 151), if desired and available. The data can also interface with an open ID credential exchange/trusted framework (block 152).

Figure 3A:
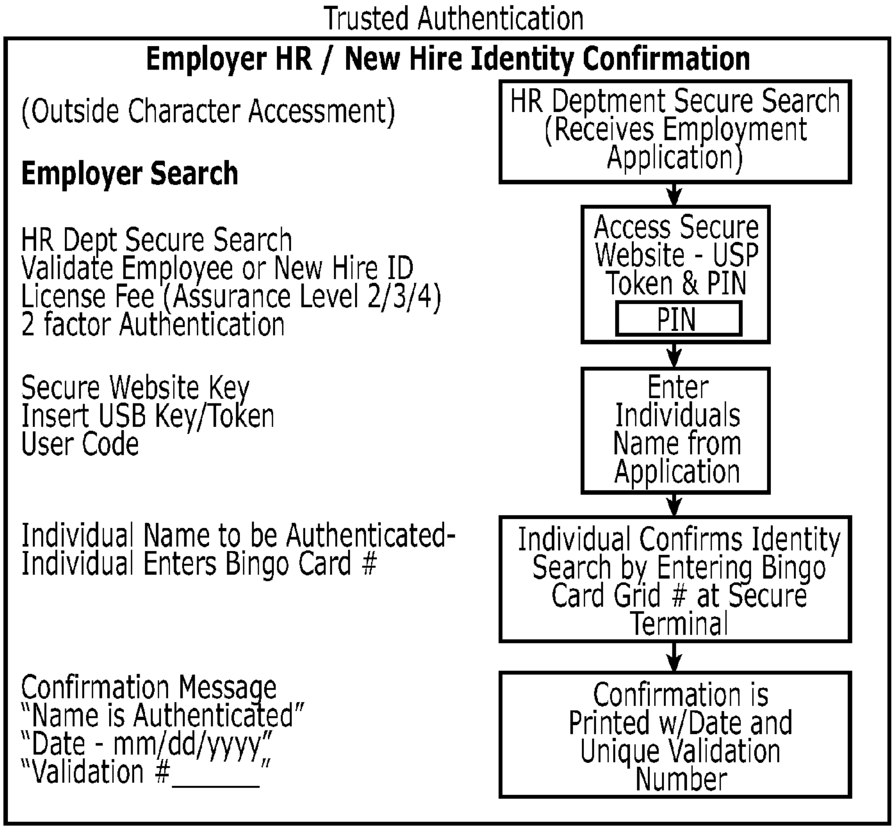
FIGS. 3A-3C are block diagrams illustrating trusted authentication, including employer/new hire identity confirmation (FIG. 3A), hospital search/emergency department (FIG. 3B), and registered first/volunteer responders (FIG. 3C)
Figure 3B:
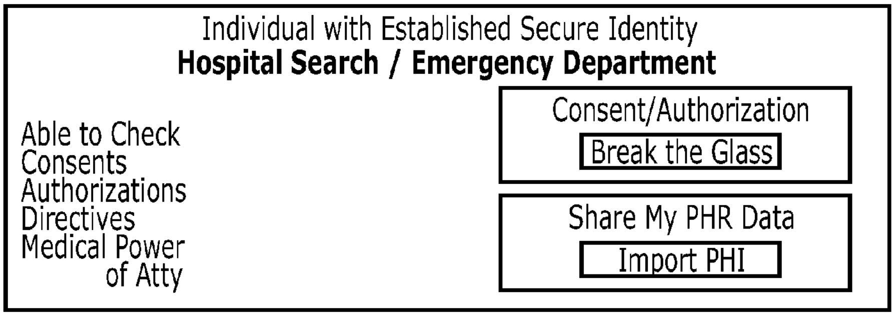
Figure 3C:

FIGS. 3A-3C illustrate the three types of trusted authentication: employer/new hire identity confirmation (FIG. 3A); hospital search/emergency department (FIG. 3B); and registered first/volunteer responders (FIG. 3C).

Figure 4:
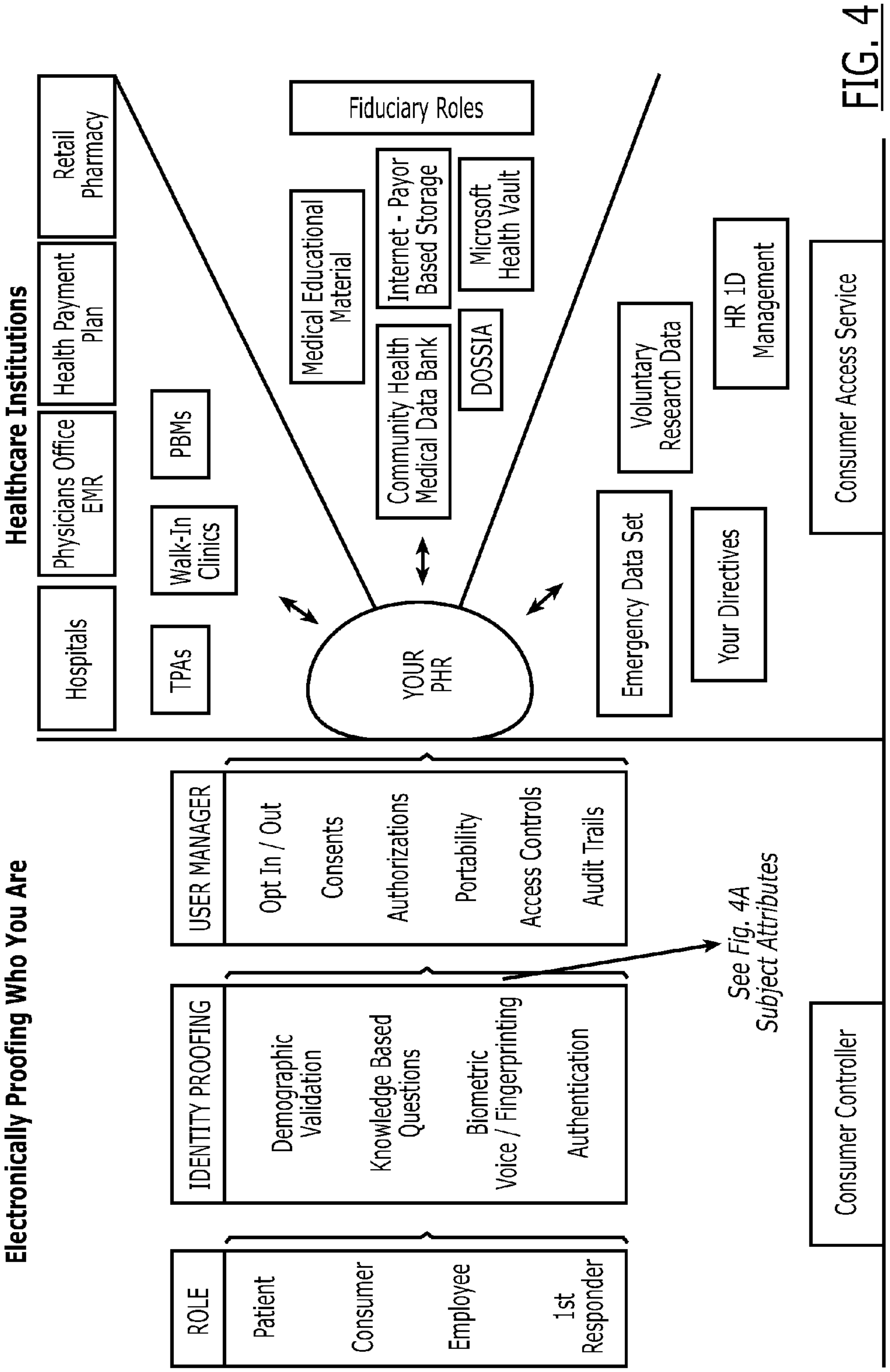
FIG. 4 is an authentication flowchart of one role-based identity proofing system illustrating an interaction of a personal health record with a healthcare institution.

FIG. 4 is a flowchart of role-based identity proofing and the interaction of a personal health record (PHR) in order to populate the Emergency Data Set (FIG. 8) and to make available to emergency responders and hospital emergency departments. I also provides a platform to send and receive health information for doctors and healthcare institutions. Data flow that is controlled by the consumer (left-hand side) is shown as contributing to the participant's PHR, which informs the consumer access service of the network, the ability to receive alerts, notices or copies of medical records or emergency reports from providers, a hospital or a clinic and story the PHI in their health data repository FIG. 4A provides the participant with role based and privacy attributes so they can control, share and manage their health information.

Figure 5:
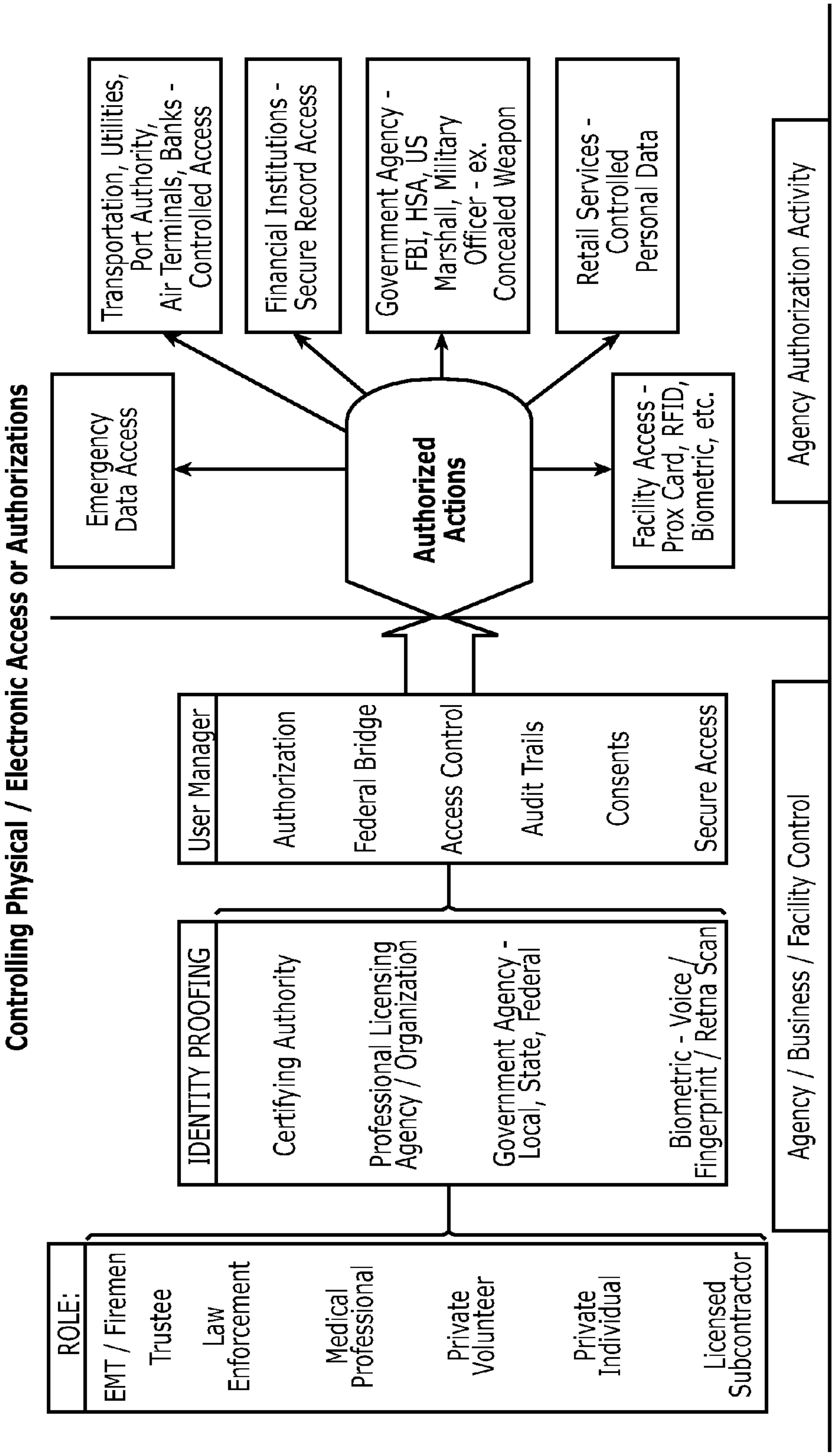
FIG. 5 is a flowchart illustrating a controlling physical/electronic access or authorizations.

FIG. 5 is a flowchart for controlling physical/electronic access or authorizations. Here are shown the different roles of the participants, leading to their respective authorized actions and access that interface with the participant.

In use, upon the occurrence of an accident, for example, typically the police are the first to arrive and notify emergency medical services. An ambulance can be dispatched, and the police attempt to identify an unconscious/unresponsive victim. This can be attempted using the motor vehicle registration records, such as VIN#, Tag#, or DL #. The vehicle identification number is used to query a federated emergency contact registry (for example, NLETS), to obtain the vehicle owner emergency contact name(s) and telephone number(s). These data are passed to the emergency responders, who can search systems for possible historic patient data.

In a particular embodiment, the VIN# registry can comprise a stand-alone system that interfaces with a state's driver's registry and interface with NLETS. An individual who registers his/her VIN# can voluntarily elect an "alert function," enabling a law enforcement office to be alerted via, for example, a red flag, that emergency medical data are available and can alert an EMT. The user can also create an emergency medical data set, using their PHR, and elect not to have a flag posted.

The emergency medical data can comprise a subset of a personal health record (PHR). These data should preferably be stored on a separate secure registry, which can only be accessed by a licensed emergency professional (e.g., EMT, nurse, fire EMT, physician, ER staff, trauma center personnel). An identifying and permission-granting technology such as a voluntary health ID (VHID) can be incorporated. As illustrated in FIG. 3C, a separate registry can be provided for licensed emergency medical professionals.

If the victim's identity is established and has consented, in advance, to use their functional and privacy attributes to make Emergency Medical Data available in case of an emergency, a membership in the network is ascertained, in which case an emergency dataset is provided to the healthcare worker. The patient can then be treated at the scene and in the hospital in a more informed manner. The NLETS data are also used to make contact with those listed in the emergency contact registry.

Consent documents can also be included in the system, such as, but not intended to be limited to, VIN# ERCont/driver's license ERCont, emergency medical dataset, "break the glass" consent/authorization, organ donation data, and DNR data.

To validate the user's demographic information at a future date, once a user is fully vetted and authenticated, a unique email address is generated that will incorporate the alpha text of their email address to the left of "@" followed by a forward slash (/) mark, at which time their validated address will be inserted excluding state and including zip code immediately followed by @. After the "@" mark will be "USPS.GOV>" (sample: jkragh/1024orangeaceorlando32802@usps.gov) encrypted. At a future date both this email (address inserted) can be sent to the USPS to validate its authenticity accompanied with an attachment of a new address of the user if such applies. This process is for authenticating and revalidating an authenticated ID or "elink authentication."

In summary, the system and methods of the present invention permit the establishment of a trusted process for interoperable identity management in a distributed healthcare enterprise. The system and methods provide ID proofing, vetting, and leveraging vetted authenticated cards/tokens usable in a distributed interoperable knowledge healthcare environment.

The key principles include ID proofing, generating new identity reference/tokens, or recognizing and accepting existing ones to provide contacts and directives. A trusted process incorporates functional, institutional and privacy attributes linked to participants digital ID is included for generating an enhanced token in compliance with Federal Guidelines and Regulations and established policies. Real-time authentication or verification of identity are coupled with privileges and role-based access control with attributes are provided, as well as "rules-of-the-road" and "best practices" as applicable across multiple trusted domains, medical professional, and healthcare user communities to address medical emergencies and disasters. Communities and organizations define their own policies, rules, privileges, and criteria, which can be distributed. HIPAA, state, and stimulus guidelines are followed, offering a common foundation for recognizing authenticated identities in a variety of public and private healthcare settings across the national landscape, and even internationally.

Clear definitions of trusted "rules of the road" and recommended policies are provided for adoption in healthcare, and the ability to apply the rules consistently within local, enterprise, and federated architectures. This provides a cross-cutting functionality, which addresses the typically inconsistent methodologies inherent in current healthcare facilities. A foundation for privilege and attribute management is provided, which can include an expanded reach with business associate agreements, certified personal health records, and certified electronic medical records.

Further, consistent implementation is balanced with potential cost/risks. The system and methods have appropriate levels of trust/assurance, with both identity and assigned attributes. A common foundation is also provided for education and promotion, and a cost-effective process for a more common risk-management framework.

An exemplary privacy class matrix is depicted in FIGS. 6, 6A, 6B and 6C illustrating elections that can be made by the user regarding privacy levels (to share all data, restrict data sharing, share with restricted access, no sharing of data, and emergency-only sharing of data). Any number of classes can be devised for each of these privacy levels, so that a user can select a privacy level over a multitude of domains, such as a disease state.

Recognizing that not one size fits all in proving one's identity, an organization or individual will have a choice in selecting the strength and integrity of the ID proofing plan they will go through, as discussed above. Following the NIST guidelines, one can select a strong authenticated ID (FIG. 7) Plan A that requires more steps in the ID proofing process and represents a higher level of "trust" than if one elects Plan B, which represents a less rigorous level of identity proofing, resulting in a moderate level of authenticated trust and therefore requiring a fewer number of steps as in Plan A. If a lower level of a trusted ID is desired (below Plan B) and only a few steps in the identity proofing process are needed, then Plan C would be utilized. A group or an organization may also elect to have a customized program of steps (FIG. 7) that must be used to achieve a passing score to achieve a desired authentication level.

Typically, each plan will have a scoring process associated with it in order to achieve a plan-designated authentication scoring level. An individual will know steps in advance that will assist in helping one achieve a designated score that can be independently validated and audited. The resulting score of an identity-proofing process then results in a pass or no-pass score.

FIG. 8 is an exemplary emergency medical data set layout of the present invention digitally or electronically signed by someone with access to the entire record.

FIG. 9 is a portion of the data set of FIG. 8, with the emergency medical data set hidden from view.

FIG. 10 is an exemplary screen shot of an exemplary portal for generating data via a user's personal health record.

By way of further example, the forgoing matrix graphics of FIGS. 4A, 5A, 6A, 6B and 6C as representing relational steps associated with a patient/actor using their Digital ID in granting access and viewing privileges to their PHI. When a cell in one of the matrixes is selected (a Column-Row alpha-numeric construct) by a patient, the cell and line item selected within the cell generates a unique algorithmic attribute (4A.c1001.a.rB001.1L200.exd__________.t, by way of example). This patient centric process provides a platform for adapting to the changing landscape of technology, Federal Mandates, Guidelines and Standards while generating e-audit trails. This harmonizing sequence of linking attributes between Actors, Objects, Functions and Infrastructure patient granted Access Control functions coupled with Privacy viewing and PHI sharing privileges.

By way of further example, in case of an emergency a patient wants EMT's and Hospital Emergency Departments to have timely access both an Emergency Medical Data set and an Emergency Contact list. To achieve this goal, a consumer/patient who has been authenticated and has a Digital ID would consider providing consent on what specific information the consumer/patient wants shared with in the medical community defining specific events, titles and institutions as to what specific data is shared. In this scenario, the consumer/patient starts with graphic of FIG. 4 (macro view) and FIG. 4A, a detailed view, which address how an individual engages the healthcare system in sharing emergency PHI. The patient selects cell 1B line 2 which is 'EMT's' along with 3B line 2 (ER Medical Data Set) and 4G line 2 (Emergency Contacts) and in the process a unique algorithmic attribute is initiated.

A health care community/enterprise functions a separate yet parallel set standards and guidelines for engaging and sharing PHI. They too can gain access, in emergencies, access to critical health data and in some cases, operating federal guidelines, they can 'brake-the-glass' to access PHI without violating privacy laws. FIG. 5 (macro view) and FIG. 5A a detailed process on how medical professionals and EMT's gain access (using an enhanced standards based process) to access Emergency Medical Data Sets Emergency Contact information, if available. A Healthcare Community is represented by institutions, networks, system, clinics, etc. and is referred to as Objects in the standards world and are assigned attributes also. Medical professionals are defined as actors with authenticated identities (mandate) which incorporate their professional medical task and the entity they represent. In this scenario, an EMT selects the cell that defines the EMT's role as the EMT (1B line 2) along with information desired to perform their duties (emergency data and contact information): hence 3B line 2 is selected along with 4G line 2. This sets the infrastructure framework on what actors and their roles will be. Now protected health data is needed along with permission on how such should be shared.

Under HIPAA Privacy rules, the patient must provide consent as to what data they want to make available, to whom and under what conditions or events. By way of continued example, FIGS. 6 (macro view), 6A, 6B and 6C provide a sequential attribute process for enabling patient privacy consents in order to share confidential health information. This phase enables the sharing and viewing of PHI under patient defined events so the patient needs to be proactive in creating and selecting what information she or he wants shared from the health data repository. In the scenario, an EMT or ER physician/nurse must have a high degree of confidence in trusting the PHI being shared if it is to be used in clinical decision making. So a patient, using their digital ID, needs to create both an Emergency Data Set (FIG. 8) and or an Emergency Contact Set (FIG. 9) using their computerized Certified Personal Health Record and electronically signing record, making it available to EMT's and Hospital ER Departments. To provide the proper consent acknowledgments in sharing Emergency Data a patient would need to select/approve from FIG. 6A, Column C (share Emergency Medical & Contact Data), Row 1 (consent: Yes), Row 4 (acknowledge privacy rule), Row 6 (check Yes, permitting Restricted Data Sharing and Row 8 (Yes to Restricted Access). Since the patient generated their own Emergency Medical Data Set they must select and registered the type electronic device that was used to create their Emergency Data Set (such as their Personal Computer). This provides an end-to-end data integrity linkage with the accompanying attributes so Emergency medical professional can trust the integrity of PHI being shared.

Figure 6B:
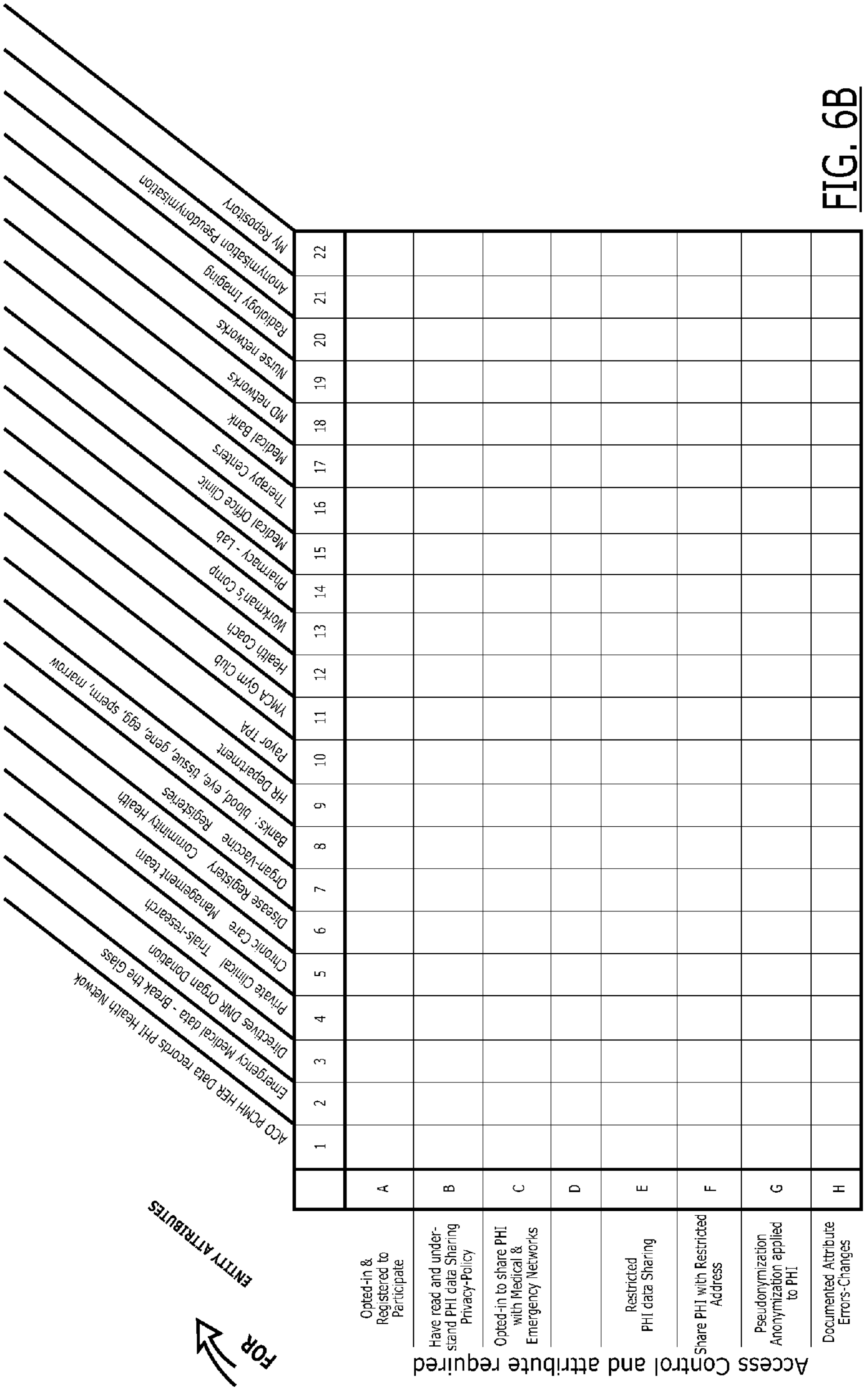
FIG. 6B illustrates parameters for sharing PHI and the entity attribute classes of Personal Health Information and defined location including by way of example, private and personal elected PHI data sharing attributes with health networks and groups including repositors, registers and designated entities.
Figure 7:
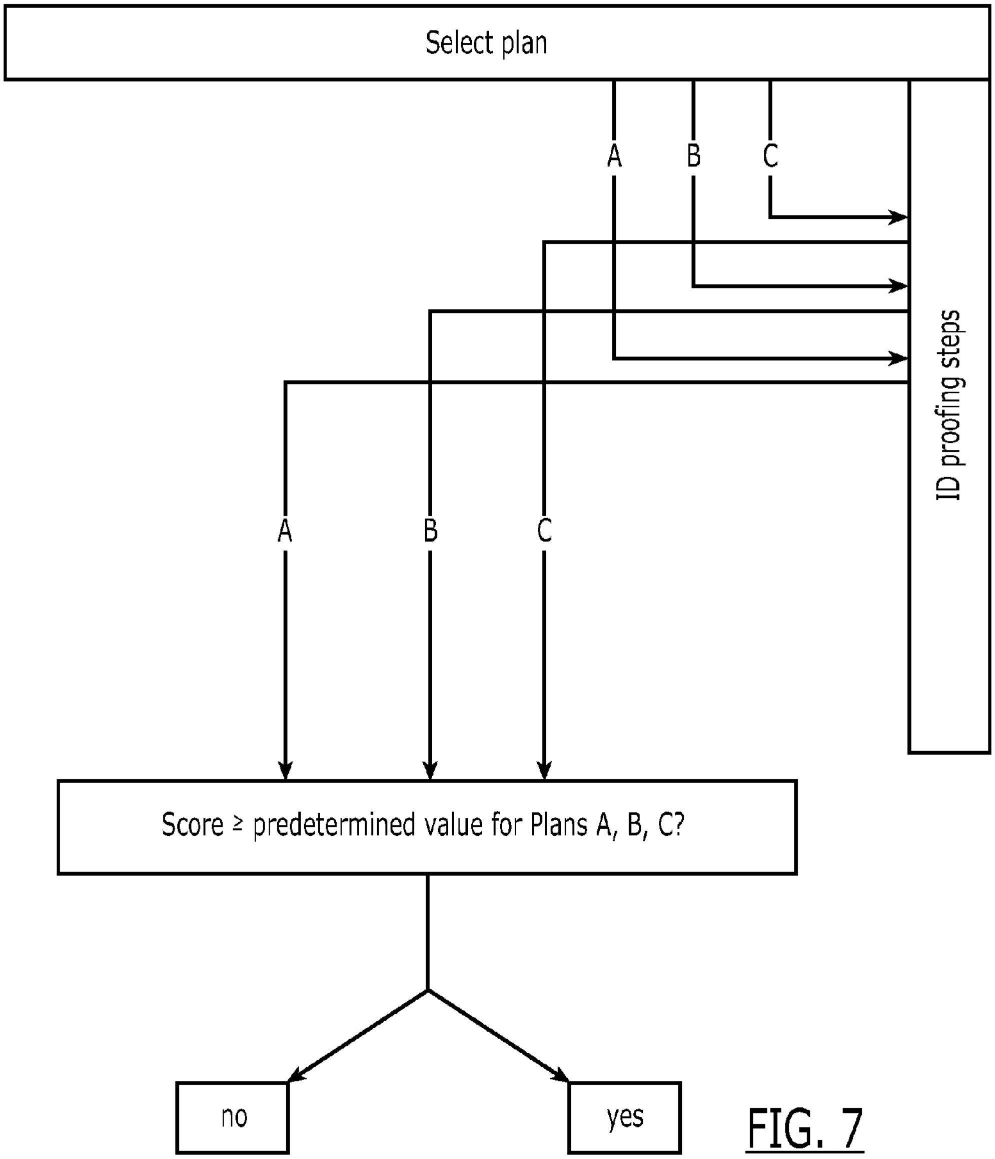
FIG. 7 diagrammatically illustrates a matrix for plan selection based upon level of authentication desired, and reflects flexibility in adopting authentication levels of assurance.

FIG. 6B links the Patient to their professional medical network or hospital system where there is an infrastructure or framework in place for sharing electronic health information and where the patient has an established relationship, agreement or contract for coordinating care and sharing PHI, specifically Emergency Medical Data. In this scenario, in FIG. 6B, Column 2 (sharing Emergency Medical Data & Break the Glass) is selected and Row A (Opt-in & have Registered), Row B (accepted PHI data sharing policy), Row C (opted-in to sharing Emergency Data), Row D (elected Restricted Access to PHI), and Row E (elected Restricted PHI Data Sharing) are checked as is 1A Electronic Health Record data allowing EHR emergency to be shared with the patient's health network.

FIG. 6C specifically defines what type of protected health data can be shared and with whom, by title and or name and in what time frame if there is a defined limit. In this scenario the FIG. 6C-A6 box is checked for EMT and Hospitals, ACO's PCMH's so emergency health data is shared with them and by checking A4 the same information will be shared with the patient's personal physician. (A medical directory of names would be provided). Additionally, the patient elects to have a copy of any Emergency Medical Record placed in their "Health Data Repository", Y1, so it too is current. The health data repository is a patient's personal health data secure file containing their PHI and electronic copies of the EHR documents that medical providers have shared with the patient.

By way of further example, FIG. 6A-6B illustrates a voluntary digital ID privacy attribute matrix relating FIGS. 6A, 6B and 6C that collectively interface with personal privacy selections for protecting health information, by way of example, associated with features, functions and access roles assigned as per FIGS. 4A and 4B and controlled by the patient, alternatively referred to as the actor or the user.

Further, it will be understood by those of skill in the art that flowcharts and block diagrams herein described may illustrate architecture, functionality, and operation of possible implementations of systems, methods and computer program products according to various embodiments. Therefore, it will be understood that each block in the flowchart or block diagram may represent a module, segment, or portion of code, which comprises one or more executable computer program instructions for implementing the specified logical function or functions. Further, some implementations may include the functions in the blocks occurring out of the order as herein presented. By way of non-limiting example, two blocks shown in succession may be executed substantially concurrently, or the blocks may at times be executed in the reverse order, depending upon the functionality involved. It will also be noted that each block of the block diagrams and flowcharts, and combinations of blocks in the block diagram and flowchart illustrations, may be implemented by special purpose hardware-based systems that perform the specified functions or acts, or combinations of special purpose hardware and computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart and/or block diagram. These computer program instructions may also be stored in a computer readable medium that may direct a computer, other programmable data processing apparatus, or other devices to function in a particular manner, such that the instructions stored in the computer readable medium produce an article of manufacture including instructions which implement the function or act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Aspects of various embodiments as herein presented, by way of example, may be embodied as a system, method or computer program product, and accordingly may take the form of a hardware embodiment, a software embodiment (including firmware, resident software, micro-code, and the like) or a combination thereof that may generally be referred to as a circuit, module or system. Furthermore, aspects of various embodiments may take the form of a computer program product embodied in one or more computer readable media having computer readable program code embodied thereon.

It is also understood that a computer implemented method as may herein be described operates with readable media relating to non-transitory media, wherein the non-transitory computer-readable media comprise all computer-readable media, with the sole exception being a transitory, propagating signal.

Any combination of one or more computer readable media may be utilized. A computer readable medium may be a computer readable signal medium or a computer readable storage medium. A computer readable storage medium may be, by way of non-limiting example, an electronic, magnetic, optical, electromagnetic, infrared, or semiconductor system, apparatus, or device, or any suitable combination of the foregoing. More specific non-limiting examples of the computer readable storage medium may include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that may contain, or store a program for use by or in connection with an instruction execution system, apparatus, or device.

A computer readable signal medium may include a propagated data signal with computer readable program code embodied therein, by way of non-limiting example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that may communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, and the like, or any suitable combination thereof. Computer program code for carrying out operations for aspects of various embodiments may be written in any combination of one or more programming languages, including an object oriented programming language such as Java, Smalltalk, C++ or the like and conventional procedural programming languages, such as the C programming language or similar programming languages. The program code may also be written in a specialized language. The program code may execute entirely on the user's computer, partly on the user's computer, as a stand-alone software package, partly on the user's computer and partly on a remote computer, or entirely on the remote computer or server. The remote computer may be connected to the user's computer through any type of network, including a local area network (LAN) or a wide area network (WAN), or the connection may be made to an external computer, by way of non-limiting example, through the Internet using an Internet Service Provider.

Having now described the invention, the construction, the operation and use of preferred embodiments thereof, and the advantageous new and useful results obtained thereby, the new and useful constructions, and reasonable equivalents thereof obvious to those skilled in the art, are set forth in the appended claims.

That which is claimed is:

1. A computer implemented method for verifying and validating identity of a user for enrollment of the user in a secure personal dataset accessing system including a secure personal dataset, the computer implemented method comprising:

electronically receiving a personal dataset including identifiable attributes of a user into a computer;

using the computer, electronically verifying through an independent party authenticity of an asserted identity of the user including the identifiable attributes of the secure personal dataset;

electronically verifying the personal dataset with a relying party that contributed to the secure personal dataset;

automatically capturing at least one biometric identifier of the user on the computer for validating the identifiable attributes of the user, wherein the validating includes confirming the asserted identity matches the identifiable attributes;

generating a digital security element as a result of the verifying and validating of the identifiable attributes;

electronically receiving a password into the computer by the user employing the digital security element;

creating a registry having the identifiable attributes for the user stored within the registry;

automatically assigning a unique electronic address in the registry for the user using the computer in response to the password; and transmitting the digital security element to the user from the computer, the digital security element enabled for granting electronic access to the personal dataset relating to the user, the personal dataset having been authenticated through the verifying and validating steps.

2. The computer implemented method according to claim 1, further comprising providing an e-audit trail having a traceable electronic enterprise infrastructure and bench mark performance indicator for the digital security element generating step.

3. The computer implemented method according to claim 1, wherein the personal dataset comprises date of birth, gender, and at least a portion of a government issued identification number of the user, address and citizenship, and wherein the electronically verifying comprises transmitting the date of birth, the gender and the at least the portion of the identification number to be a third party verification system for validating the date of birth, the gender and the at least the portion of the identification number.

4. The computer implemented method according to claim 3, wherein the government issued identification number includes at least one of a social security number, driver's license, passport, a Federal PIV card, and a US Postal Service number issued digital credential with postmark acceptable to the third party.

5. The computer implemented method according to claim 1, wherein the personal dataset comprises a designated mailing address and the verifying compromises accessing a postal service database and determining a length of time during which the designated mailing address has been valid.

6. The computer implemented method according to claim 1, further comprising:

providing a list of employee names by an organization for a vetting of the list of the employee names;

authenticating the organization;

providing each employee with a link and a unique password to a secure site as an initial validating source;

permitting the employee to access the secure site during a designated time period; and enrolling the employee by at least one of name, employee identification number, magnetic stripped card, designated membership card, and secondary validating source from which to initiate the verifying.

7. The computer implemented method according to claim 1, wherein the personal dataset comprises a personal telephone number, and the verifying comprises electrically determining that the personal telephone number is associated with a designated address through a carrier of the personal telephone number.

8. The computer implemented method according to claim 1, wherein the electronically verifying authenticity step comprises verifying a payment card through a third party with a Yes or No response regarding good standing.

9. The computer implemented method according to claim 1, wherein the verifying is placed on hold when the user fails to meet a preselected score value, and wherein an electronic document is sent to the user.

10. The computer implemented method according to claim 1, wherein the personal dataset comprises licensing information and the electronic verifying step comprises transmitting the licensing information to a credentialing service for verification.

11. The computer implemented method according to claim 1, wherein the verifying step comprises automatically placing an out-of-bound telephone call to the user from the computer for verifying a telephone number and recording a presentation with a biometric voice print of the call provided by the user for providing at least a portion of the personal dataset.

12. The computer implemented method according to claim 1, wherein the verifying step comprises the user providing a photograph and a description of the photograph.

13. The computer implemented method according to claim 1, wherein the electronically verifying the identifiable attributes is followed by compiling an identity attribute profile for the user.

14. The computer implemented method according to claim 13, further comprising the user generating an attribute bundle representing a select number of designated user identification attributes necessary for meeting a transaction requirement.

15. The computer implemented method according to claim 1, further comprising generating a unique index number and assigning the index number to the digital security element.

16. The computer implemented method according to claim 1, further comprising generating a voluntary health index number and assigning the voluntary health index number to the user.

17. The computer implemented method according to claim 16, further comprising forming an attribute health data repository comprising health data defined attributes that correspond to object attribute groups.

18. The computer implemented method according to claim 17, further comprising controlling access to the health data repository for use by a service provider, wherein upon an authenticated consent by the user, emergency medical and contact data are made available to the service provider.

19. The computer implemented method according to claim 17, wherein the health data repository comprises demographic, insurance and vehicle information data, electronically signed then captured as an emergency contact dataset as a read-only packet and then securely posted.

20. The computer implemented method according to claim 1, further comprising sharing the personal dataset by the user, wherein the sharing comprises permitting access the personal dataset within the registry for a preselected set of the identifiable attributes, and wherein the sharing requires authenticating a sharing party.

21. A computer implemented method for accessing a secure personal database, the method comprising:

creating a registry for storing a secure personal database having identifiable attributes of a user;

electronically receiving a personal dataset including identifiable attributes of a user by a processor;

electronically verifying authenticity of an asserted identity of the user including the identifiable attributes of the secure personal dataset through an independent party;

electronically verifying the personal dataset with a relying party that contributed to the secure personal dataset;

storing the personal dataset on the secure personal database in the registry;

validating the identifiable attributes of the user, wherein the validating includes confirming the asserted identity matches the identifiable attributes;

generating a digital security element as a result of the verifying and validating of the validated identifiable attributes;

enabling the digital security element for granting electronic access to the personal dataset on the secure personal database stored within the registry;

designating privacy levels of assurance for access to the personal dataset by the user; and authorizing access to the personal dataset by the user for an authorized member of the registry.

22. The computer implemented method according to claim 21, wherein the privacy levels of assurance designating comprises establishing at least one of emergency medical data access and emergency contact data access for authorized access the at least one of the emergency medical data access and the emergency contact data access.

23. The computer implemented method of claim 22, further comprising requesting access to at least one of the emergency medical data and the emergency contact data by a licensed emergency professional as the authorized member.

24. The computer implemented method of claim 21, wherein the privacy levels of assurance designating comprises designating at least one of a first level of assurance permitting access to the registry for all emergency medical data and all emergency contact data, a second level of assurance permitting access to the registry for preselected emergency medical data and all emergency contact data, and a third level of assurance permitting access to the registry for only the emergency contact data.

25. The computer implemented method of claim 24, wherein the access authorizing comprises authorizing access to the first level for Federal Emergency Management Agency (FEMA), as an authorized registry.

26. The computer implemented method of claim 21, further comprising accessing the personal dataset by the authorized member.

27. The computer implemented method of claim 26, wherein the accessing comprises accessing the personal dataset using a secure mobile device.

* * * * *